| (12) | United States Patent | (10) Patent No.: | US 11,003,352 B2 |
|---|---|---|---|
| | Nielsen et al. | (45) Date of Patent: | May 11, 2021 |

(54) ULTRASOUND IMAGING SYSTEM TOUCH PANEL CLUSTER CONTROL INTERACTION

(71) Applicant: B-K Medical Aps, Herlev (DK)

(72) Inventors: Torben Svanberg Nielsen, Copenhagen (DK); John Antol, Nahant, MA (US); Kaj Dunkan, Stenlille (DK); Jesper Helleso Hansen, Copenhagen (DK)

(73) Assignee: B-K Medical Aps

( * ) Notice: Subject to any disclaimer, the term of this patent is extended or adjusted under 35 U.S.C. 154(b) by 511 days.

(21) Appl. No.: 15/529,564

(22) PCT Filed: Nov. 26, 2014

(86) PCT No.: PCT/IB2014/066365
§ 371 (c)(1),
(2) Date: May 25, 2017

(87) PCT Pub. No.: WO2016/083869
PCT Pub. Date: Jun. 2, 2016

(65) Prior Publication Data
US 2017/0322724 A1 Nov. 9, 2017

(51) Int. Cl.
*G06F 3/0488* (2013.01)
*A61B 8/00* (2006.01)
(Continued)

(52) U.S. Cl.
CPC ........ *G06F 3/04886* (2013.01); *A61B 8/4405* (2013.01); *A61B 8/465* (2013.01);
(Continued)

(58) Field of Classification Search
CPC ............... G06F 3/0482; G06F 3/04845; G06F 3/04886; A61B 8/4405; A61B 8/465; A61B 8/467
See application file for complete search history.

(56) References Cited

U.S. PATENT DOCUMENTS

| 2004/0119756 A1* | 6/2004 | Kumhyr | ................... G06F 9/451 715/837 |
|---|---|---|---|
| 2004/0119757 A1* | 6/2004 | Corley | ................ G06F 3/04817 715/837 |

(Continued)

FOREIGN PATENT DOCUMENTS

| WO | 2013046103 A1 | 4/2013 | |
|---|---|---|---|
| WO | WO-2013046103 A1 * | 4/2013 | ............. A61B 8/463 |

(Continued)

OTHER PUBLICATIONS

International Search Report for PCT/IB2014/066365, published as WO2016083869 dated Jun. 2, 2016.

*Primary Examiner* — Amare Mengistu
*Assistant Examiner* — Jennifer L Zubajlo
(74) *Attorney, Agent, or Firm* — Anthony M. Del Zoppo, III; Daugherty & Del Zoppo Co., LPA

(57) ABSTRACT

A method includes receiving a signal from a first touch screen control in response to invocation of the first touch screen control. The first touch screen control is a control from a first cluster of touch screen controls of a plurality of different clusters of touch screen controls of an ultrasound imaging system touch screen user interface. The method further includes identifying a type of the first touch screen control based on the signal. The method further includes obtaining a control configuration for the touch screen controls based on the type of control. The method further includes constructing a control layout for the touch screen user interface based on the configuration. The method further includes visually rendering the control layout via the touch screen user interface.

31 Claims, 12 Drawing Sheets

(51) Int. Cl.
  *G06F 3/0484* (2013.01)
  *G06F 3/0482* (2013.01)
(52) U.S. Cl.
  CPC ............ *A61B 8/467* (2013.01); *G06F 3/0482* (2013.01); *G06F 3/04845* (2013.01)

(56) References Cited

U.S. PATENT DOCUMENTS

| | | | | |
|---|---|---|---|---|
| 2009/0131793 | A1* | 5/2009 | Stonefield | A61B 8/00 600/443 |
| 2010/0064255 | A1* | 3/2010 | Rottler | G06F 3/0482 715/821 |
| 2014/0378833 | A1* | 12/2014 | Cheng | A61B 8/14 600/440 |
| 2015/0033136 | A1 | 1/2015 | Sasaki | |

FOREIGN PATENT DOCUMENTS

| | | | | |
|---|---|---|---|---|
| WO | 2014128801 | A1 | 8/2014 | |
| WO | WO-2014128801 | A1 * | 8/2014 | ......... G06F 3/04817 |

\* cited by examiner

ULTRASOUND IMAGING SYSTEM TOUCH PANEL CLUSTER CONTROL INTERACTION

RELATED APPLICATION

This application is a national filing of PCT application Serial No. PCT/IB2014/066365, filed Nov. 26, 2014, published as WO2016/083869 on Jun. 2, 2016. This application claims priority to PCT application Serial No. PCT/IB2014/066365, published as WO2016/083869 on Jun. 2, 2016.

TECHNICAL FIELD

The following generally relates to ultrasound imaging and more particular to an interaction of controls of multiple different clusters of controls of a touch panel of an ultrasound imaging system.

BACKGROUND

An ultrasound imaging system has included an ultrasound probe with a transducer, a console with an integrated or external display monitor, and a user interface. The transducer transmits an ultrasound signal into a field of view and receives echoes produced in response to the signal interacting with structure therein. The echoes are conveyed to the console and are processed, producing images of the scanned structure, which may be visually presented through the display monitor.

The display monitor may include a cathode ray tube (CRT), a liquid crystal display (LCD), a light emitting diode (LED) display, and/or other type of display. The display monitor has been a "dumb" monitor with no processor or processing capabilities and that is simply an output device that displays images and other information (e.g., transducer frequency, gain, etc.). The user interface has included a keyboard or keypad with mechanical depressible buttons and/or a flat touch screen area (e.g., LCD, CRT, etc.).

The display monitor has been placed in an upright vertical position so that the clinician can look at images and/or the other information displayed via the display monitor. The user interface has been placed in a generally horizontal position, approximately perpendicular to the upright vertical position. This arrangement is similar to that of a desktop computer monitor and corresponding keyboard. The user controls features such as gain, zoom, pans, etc. with the controls of the user interface.

Unfortunately, with such a user interface/display monitor arrangement, where the user interface includes a touch screen with a flat surface, it may not be readily easy for the user to locate and/or operate touch sensitive controls of the user interface while observing an image and/or patient. Rather, the user may have to look away from the image and/or patient and down at the user interface to find and/or operate the control, adding complexity and inefficiency to the procedure.

SUMMARY

Aspects of the application address the above matters, and others.

In one aspect, a method includes receiving a signal from a first touch screen control in response to invocation of the first touch screen control. The first touch screen control is a control from a first cluster of touch screen controls of a plurality of different clusters of touch screen controls of an ultrasound imaging system touch screen user interface. The method further includes identifying a type of the first touch screen control based on the signal. The method further includes obtaining a control configuration for the touch screen controls based on the type of control. The method further includes constructing a control layout for the touch screen user interface based on the configuration. The method further includes visually rendering the control layout via the touch screen user interface.

In another aspect, an ultrasound imaging system includes a touch screen user interface of the ultrasound imaging system. The touch screen user interface includes a touch panel. The touch screen user interface further includes a touch screen controller of the ultrasound imaging system configured to display a plurality of different clusters of controls in one of a plurality of different configurations depending on a presently active control of the controls.

In another aspect, a touch screen user interface includes a touch panel with an active region configured to visually display different clusters of touch sensitive controls, each cluster controlling different ultrasound imaging operations of the ultrasound imaging system. A control of the active region generates a control single for an ultrasound imaging operation in response to invocation of the control. The touch screen user interface further includes a touch screen controller of the ultrasound imaging system configured to display the different clusters of touch sensitive controls on the active region in one of a plurality of different configurations in response to a signal from a currently employed control.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
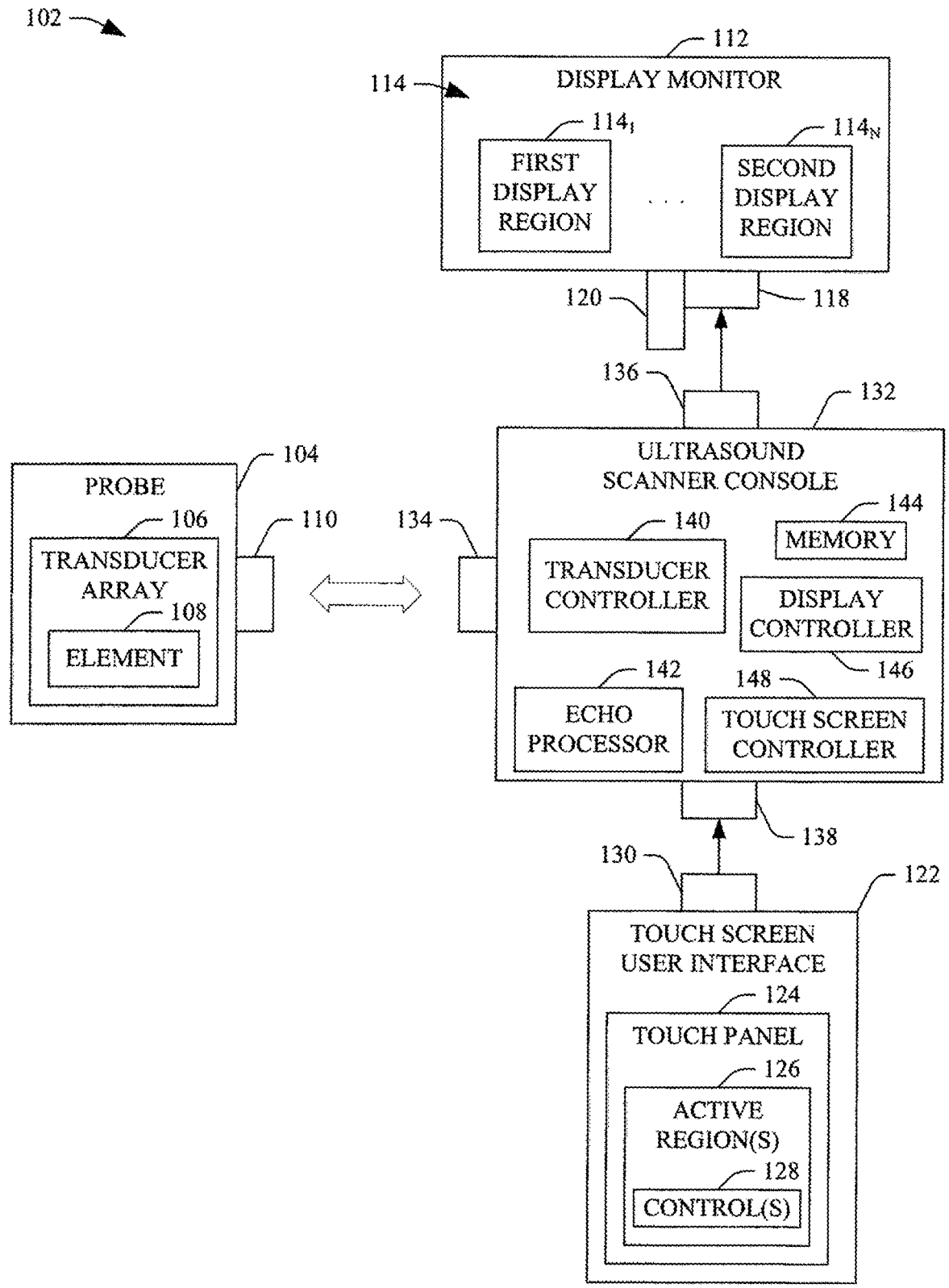
FIG. 1 schematically illustrates an example ultrasound imaging system with a touch screen user interface.

FIG. 1 schematically illustrates an ultrasound (US) imaging system 102.

The ultrasound imaging system 102 includes a probe 104 with a one-dimensional (1D) or two-dimensional (2D) transducer array 106 with at least one transducer element 108. Suitable array configurations include, but are not limited to, linear, curved (e.g., concave, convex, etc.), circular, etc., full populated or sparse, etc. The probe 104 further includes a console interface 110, which may include a connector (e.g., an electro-mechanical device for joining electrical circuits) and/or wireless transceiver.

The ultrasound imaging system 102 further includes a display monitor 112. The display monitor 112 can be a cathode ray tube (CRT), a liquid crystal display (LCD), a light emitting diode (LED), and/or other display monitor. The display monitor 112 includes a display area 114 with a multiple sub-display regions $114_1, \ldots, 114_N$, where N is a positive integer. The display monitor 112 further includes a console interface 110, which may include a connector (e.g., an electro-mechanical device for joining electrical circuits) and/or wireless receiver.

The display monitor 112 can be affixed to a support 120 (as shown in FIG. 1) such as a stand, a bracket, etc. that rests on or is affixed to a surface (e.g., a desk, a table, etc.) and holds the display monitor 112 in a generally upright vertical viewing position. In another instance, the support 120 can be a wall bracket that mounts to a wall, a ceiling, etc., thereby indirectly mounting the display monitor 112 thereto. Other supports are also contemplated herein. The support 120 may be configured to rotate, tilt, translate, and/or otherwise move, which selectively allows for spatially orienting the region 114.

The ultrasound imaging system 102 further includes a touch screen user interface 122. The touch screen user interface 122 includes a touch panel 124. At least a sub-portion of the touch panel 124 includes one or more active regions 126 with one or more touch sensitive control(s) 128 such as a time-gain control (TGC), a mode (e.g., 2D, 3D, 4D, etc.) selector control, a CINE control, a measurement control, a zoom control, a depth control, a focus control, etc. The touch panel 124 may include a resistive, a capacitive, an acoustic, an infrared, an optical, a piezoelectric, and/or other region. Furthermore, the touch panel 124 may include an LCD, thin film transistor (TFT) LCD, organic light-emitting diode (OLED), and/or other display.

The one or more controls 128, in one instance, are kept in a normally de-activate state, but are activatable. A de-activated control 128, when actuated by a gesture (e.g., a press, a swipe, a touch, etc.) on the control 128 with one or more fingers, a stylus, a glove, etc., transitions to an active state. An activate control 128, when operated, generates an electrical signal corresponding to the operation of the control 128. Generally, when a control 128 is active, one or more other non-active controls transition to a non-activatable state. In a variation, one or more controls can be kept in a normally active state. In this variation, the normally active control may transition to a de-active state in response to activation of another control, a gesture over the control, an input signal including a control signal that de-activates the control, etc.

As an example of activation and operation, a gain control is activated by touching the control and then the gain is increased or decreased (i.e., operated) through the control through a predetermined gesture. For example, circling clockwise, sliding over in direction, etc. the gain control with a suitable object increases gain, and circling counter-clockwise, sliding in another direction, etc. over the gain control with the suitable object decreases gain. A reset control may be provided to quickly return on or more of the touch controls 128 to the initial or starting conditions. An active control can be configured to automatically transition back to a de-active state, e.g., in response to lapse of a pre-determined length of time of inactivity, activation of another control 128, on demand, etc.

Figure 2:
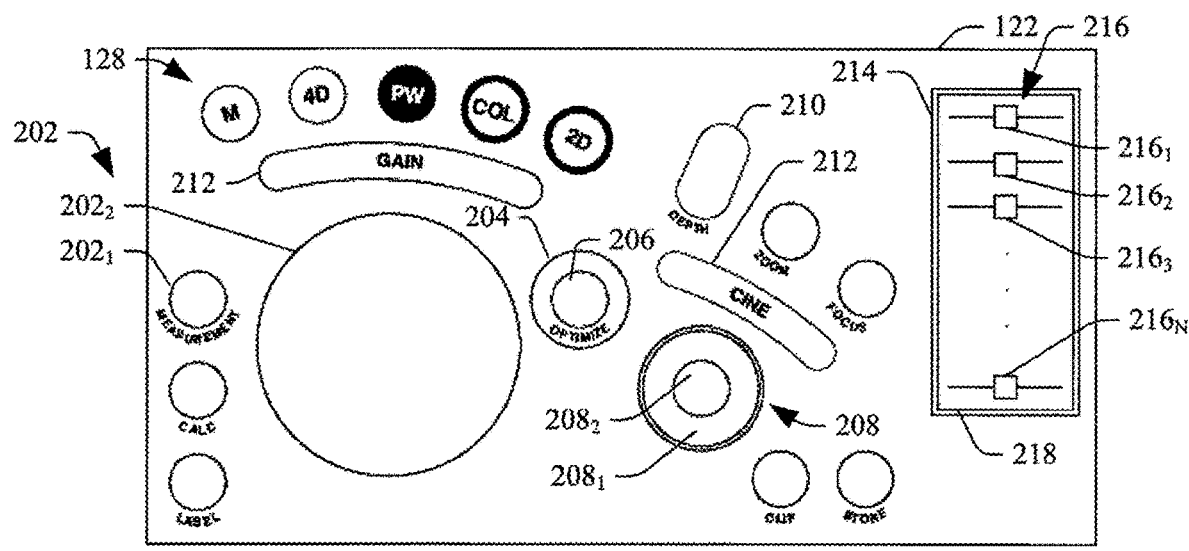
FIG. 2 illustrates an example of a cluster of controls for the touch screen user interface.
Figure 3:
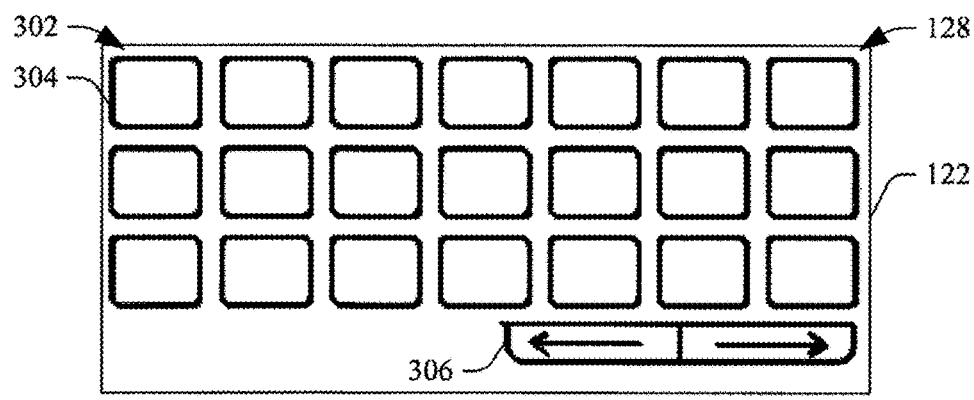
FIG. 3 illustrates another example of a cluster of controls for the touch screen user interface.
Figure 4:
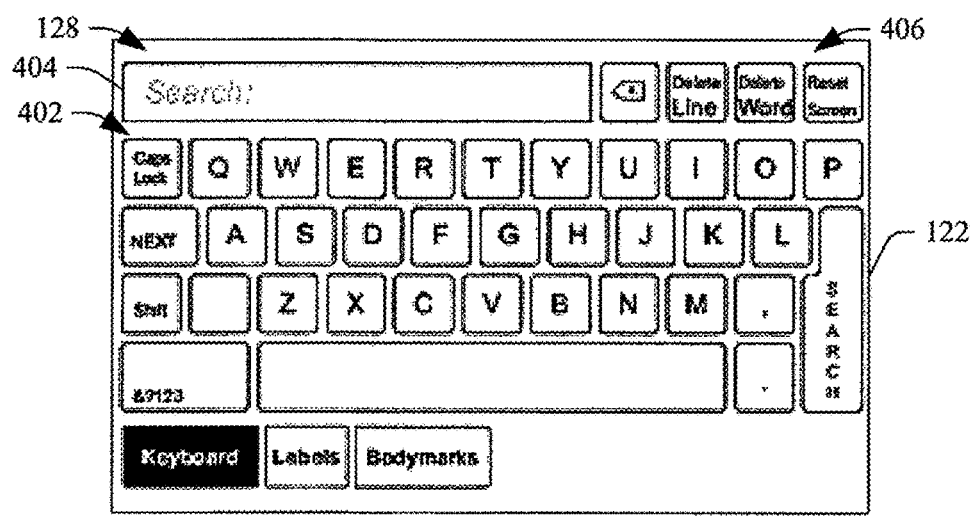
FIG. 4 illustrates another example of a cluster of controls for the touch screen user interface.

Briefly turning to FIGS. 2, 3 and 4, non-limiting examples of the touch screen user interface 122 are illustrated.

In FIG. 2, the controls 128 include circular shaped controls 202 including one control $202_1$ with one diameter and another control $202_2$ with a different larger diameter, a ring shape control 204 with a non-active area 206 in the hole of the ring, concentric controls 208 including one control $208_1$ surrounded by another control $208_1$, a rectangular control 210 with rounded edges, and curved rectangular controls 212 with rounded edges. A control 214 includes a plurality of touch activated slides $216_1, 216_2, 216_3, \ldots, 216_N$, collectively referred to herein as virtual slides 216, which reside in a recess 218 in the touch panel 124. Again, the controls 128 can be activated and used by pressing, tapping, swiping, etc.

Turning to FIG. 3, the controls 128 include a two-dimensional (2D) array 302 of rectangular controls 304 and other controls 306. In FIG. 4, the controls 128 include controls 402 of a computer keyboard as well as other controls 128, such as a search box 404, and custom configure controls 406. Another example touch screen user interface 122 includes a combination of FIGS. 2, 3 and/or 4, optionally with alternative and/or additional controls. Still other controls can also include physical mechanical controls such as a trackball, a track pad, etc. Other examples of touch screen controls are described in application Ser. No. 13/748,653, filed on Jan. 24, 2013, entitled "Ultrasound Imaging System," and assigned to B-K Medical Aps, which is incorporated herein by reference in its entirety.

Returning to FIG. 1, the touch screen user interface 122 may also include visual indicators (e.g., lights, etc.), audible indicators (e.g., speakers, etc.), tactile indicators (e.g., vibration, etc.), other controls (e.g., physical mechanical buttons, physical mechanical slides, physical mechanical rotary knobs, etc.), an image display region, etc. The touch screen user interface 122 further includes a console interface 130, which may include a connector (e.g., an electro-mechanical device for joining electrical circuits) and/or wireless transceiver.

The ultrasound imaging system 102 further includes an ultrasound scanner console 132. The console 132 includes a probe interface 134, a display monitor interface 136, and a touch screen user interface 138, which, respectively are complementary to the console interfaces 110, 118 and 130. For example, the probe interface 134 is complementary to the console interface 110 in that the probe interface 134 and the console interface 110 physically engage and provide an electrical pathway between the probe 104 and the ultrasound scanner console 132. For instance, the console interface 110 may include a female connector and the probe interface 134 may include a male connector, wherein the connectors physically engage and physically connect electrodes.

The ultrasound scanner console 132 further includes a transducer controller 140. The transducer controller 140 controls excitation of the at least one transducer element 108. The transducer controller 140 also controls detection of echoes with the at least one transducer element 108. In a variation, the excitation and detection can be through separate components such as transmit and receive circuitry. The console 132 further includes an echo processor 142 (e.g., microprocessor, central processing unit, etc.) that processes detected echoes. Such processing may include generating an image, estimating flow velocity, and/or processing. The ultrasound scanner console 132 further includes a physical memory device (memory) 144, which can be used to store ultrasound data.

A controller 146 controls the information visually presented in at least one of the display regions 114 of the display monitor 112. By way of example, in one non-limiting instance, the display controller 146 renders an ultrasound image in at least one of the display regions 114. In another example, the display controller 146 renders a graphical representation of one of the controls 128 in at least one of the display regions 114. As described in greater detail below, for the latter, the display controller 146 identifies activation and/or operation of a touch control 128 and renders the graphical representation in the at least one of the display regions 114, where the graphical representation may include alpha-numeric information and/or graphics, shows a current value and/or any changes thereto, shows movement of the actual control, etc.

Generally, the graphical representation provides a virtual control of a touch control 128, on the display monitor 112, that mirrors or mimics the touch control 128 of the touch screen user interface 122 and operation of the touch control 128 through the touch screen user interface 122. The graphical representation shows in the display monitor 112, for example, where the user's finger (or other object) is located on the touch screen user interface 122 with respect to the control 128, thereby allowing the user to adjust a control 128 without looking at the control 128 on the touch screen user interface 122. In one instance, this provides a more intuitive adaptation of the touch controls, and may reduce complexity and inefficiency, relative to a configuration in which the display controller 146 does not render virtual controls on a display region of the display monitor 112.

The ultrasound scanner console 132 further includes a touch screen controller 148. The touch screen controller 148 controls display of the controls 128 in the active region 126 and an interaction between the controls. In one instance, this includes obtaining a control cluster configuration for the touch screen user interface 122 from the memory 144 and/or other memory, constructing a display with clusters of controls for the touch screen user interface based on the control cluster configuration, and visually rendering the constructed display on the touch panel 124 of the touch screen user interface 122. The rendered controls 128 operate as discussed herein, for example, in connection with at least the description of FIGS. 2, 3 and 4, and/or otherwise. For example, certain controls are rendered active while other controls are rendered inactive, depending on a current mode of operation, a current step in a sequence of steps, etc.

As discussed in connection with FIGS. 2-4, another example touch screen user interface 122 includes a combination of FIGS. 2, 3 and/or 4, optionally with alternative and/or additional controls. In such instances, different groupings of controls can be considered different clusters of controls, for example, a cluster of controls corresponding to FIG. 2, a different cluster of controls corresponding to FIG. 3, another different cluster of controls corresponding to FIG. 4, and/or one or more other different clusters corresponding to one or more other controls. The spatial arrangement of the different clusters with respect to each other and/or within the touch panel 124 can be based on a default configuration, an orientation (e.g., portrait or landscape) of the touch panel 124, a size (e.g., 19" or 15") of the touch panel 124, an active mode of operation, an active control, an expected location of the user of the touch panel 124, etc.

Figure 5:
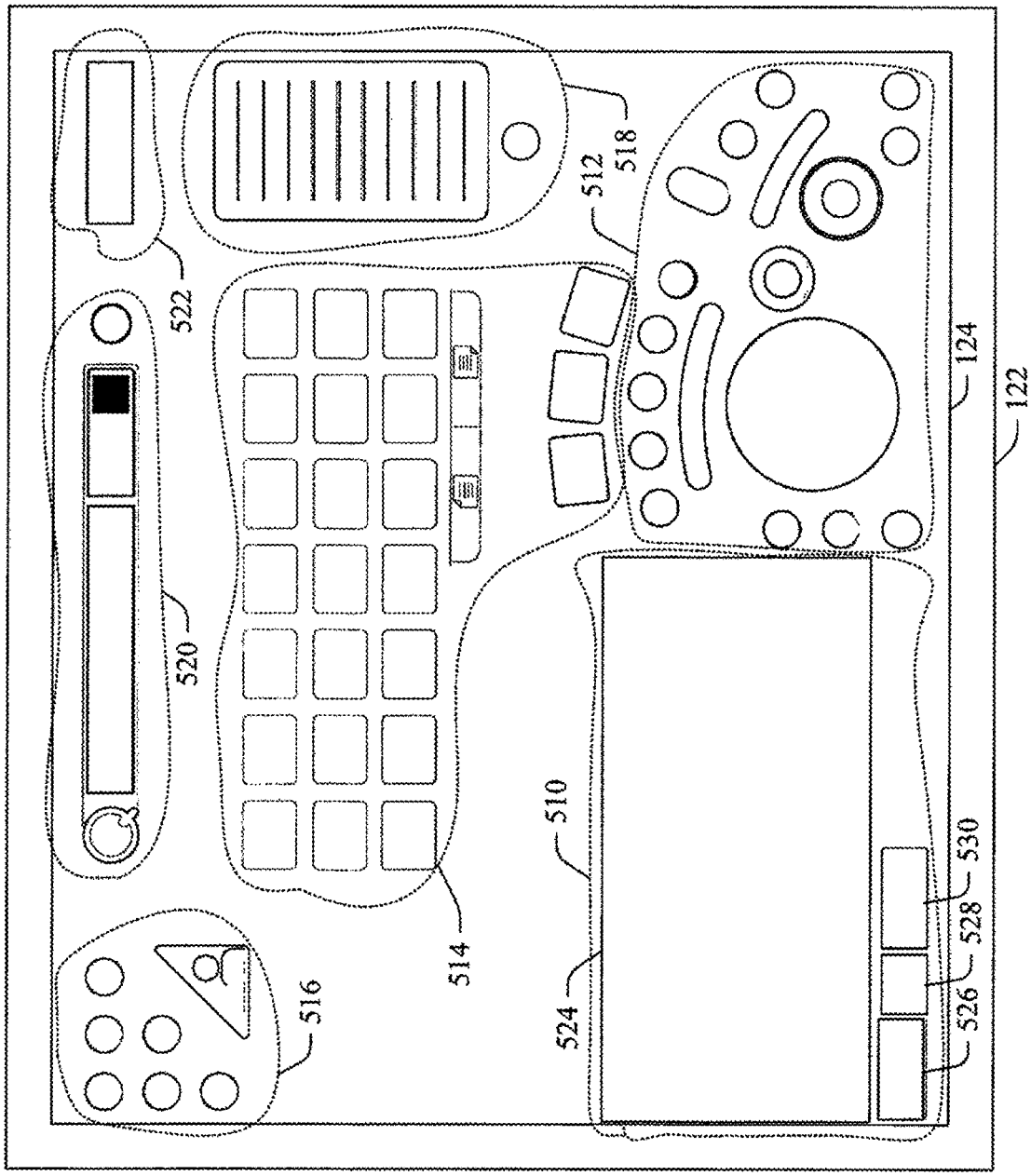
FIG. 5 illustrates an example of the touch screen user interface with multiple clusters of controls.

FIG. 5 illustrates a non-limiting example of the touch panel 124. In FIG. 5, the illustrated touch panel 124 includes an annotation cluster 510, a primary cluster 512, a contextual cluster 514, a pre/post cluster 516, a TGC cluster 518, an application cluster 520, and an exam cluster 522. Other and/or different clusters of controls are contemplated herein. Other examples of suitable cluster configurations are described in international application serial number PCT/IB2014/066363, filed on Nov. 26, 2014, and entitled "ULTRASOUND IMAGING SYSTEM TOUCH PANEL WITH MULTIPLE DIFFERENT CLUSTERS OF CONTROLS," which is incorporated herein by reference in its entirety.

Gestures that can be used with one or more of the controls described herein include, but are not limited to, a tap, multiple successive taps, a drag, a flick, a hold down, a direct touch, a press, a slide, a rotation, etc. Interaction (e.g., by a user) with a control of a cluster 510-522 may result in an interaction between controls of a same cluster and/or a control(s) of one cluster and a control(s) of one or more other clusters. Examples of such interaction include, but are not limited to, a visibility of a control, an operation controlled by a control, a status of a control (e.g., active in focus, active, activatable, inactive, etc.), a location of a control, etc.

Figure 6:
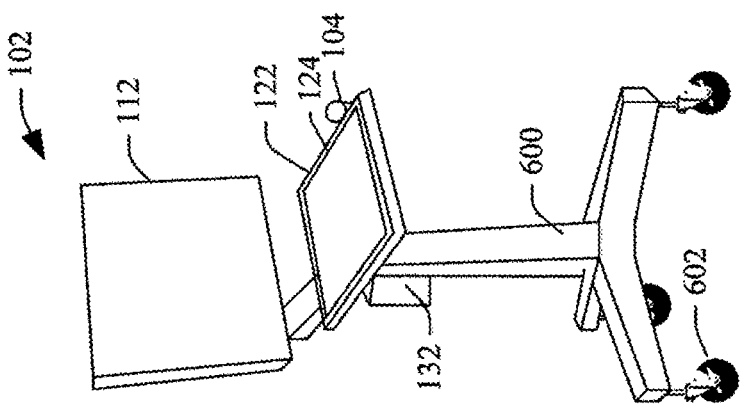
FIG. 6 illustrates an example ultrasound imaging system with the touch screen user interface of FIG. 5.

FIG. 6 shows the touch screen user interface 122 in connection with an example portable ultrasounds device. In FIG. 6, the display monitor 112, the touch screen user interface 122, the touch panel 124, and the ultrasound scanner console 132 are integrated and part of a mobile cart 600, which include movers 602 such as wheels, casters, etc. In another configuration, the ultrasound imaging system 102 rests on a table, desk, etc., and does not include movers and is not integrated into a cart, is also contemplated herein.

FIGS. 7-24 illustrate non-limiting examples of an interaction between controls of one or more of the clusters 510-522.

Figure 7:
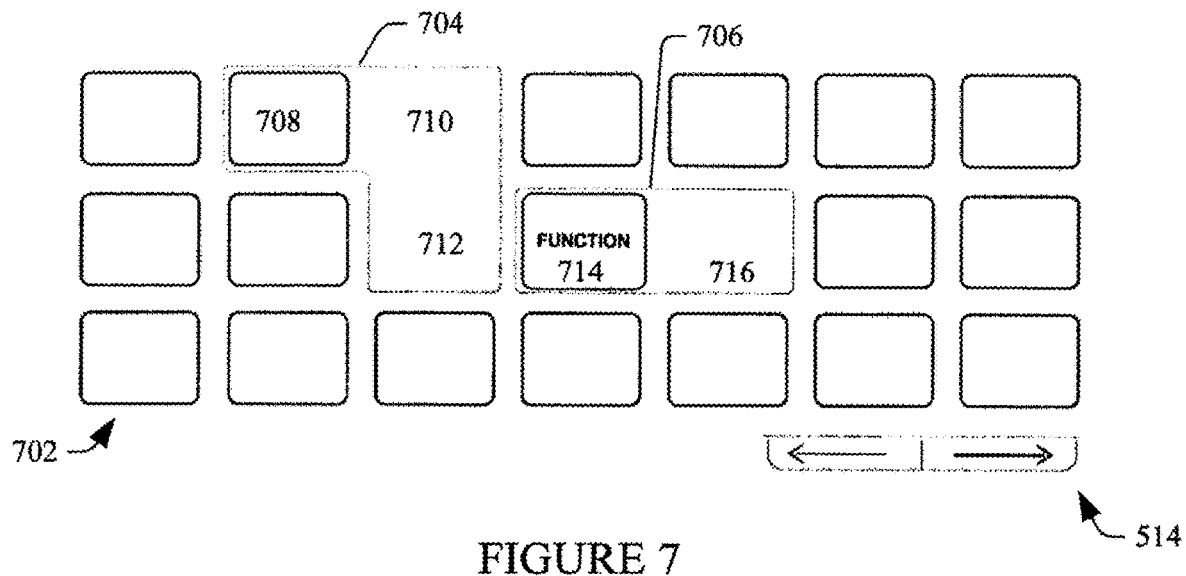
FIGS. 7 and 8 illustrate interaction of controls within a grouping of a cluster.
Figure 8:
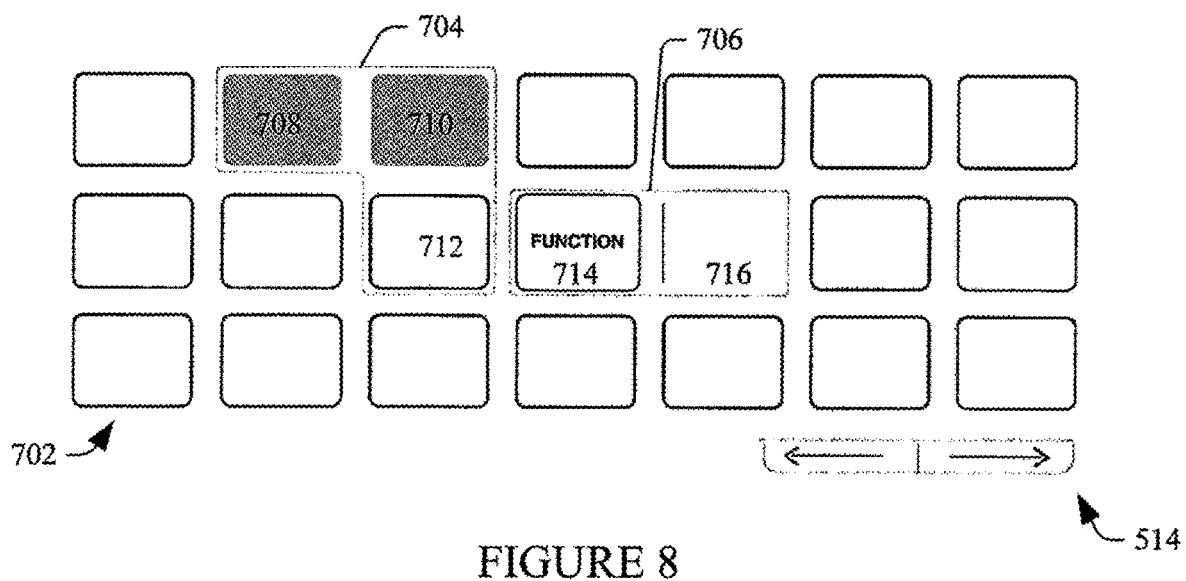

Initially referring to FIGS. 7 and 8, an example of an interaction within the contextual cluster 514 is illustrated. In FIG. 7, the contextual cluster 514 includes a plurality of controls 702, including multiple groupings of two or more of the controls 702, for example, at least a first grouping 704 and another or a second different grouping 706. Each control 702 can exist in a plurality of states, including an active (active in focus state if more than one active state), an activatable state, and an inactive state. In one instance, active (or active in focus) state represents a currently invoked control, an activatable state represents a control that can be actuated or invoked to transition to the active state, and an inactive state represents a state in which the control cannot be currently activated, but can become activatable under certain conditions.

The grouping 704 includes controls 708, 710 and 712. In FIG. 7, the control 708 is in the activatable state, and the controls 710 and 712 both are in the inactive state. In this example, the controls 710 and 712 control sub-functions that are not activatable until the control 708 is active. Transitioning the control 708 to the active state, for example, through a gesture as described herein, automatically transitions the control 710 to the active state and the control 712 to the activatable state. FIG. 8 shows the controls 708 and 710 in the active state and the control 712 in the activatable state. The grouping 706 includes controls 714 and 716. In FIG. 7, the control 714 is in the activatable state and the control 716 is in the inactive state. The control 716 controls a sub-function and is active only when the control 714 is in the active state. Controls 702 outside if the groupings 704 and 706 are in the activatable state.

Figure 9:
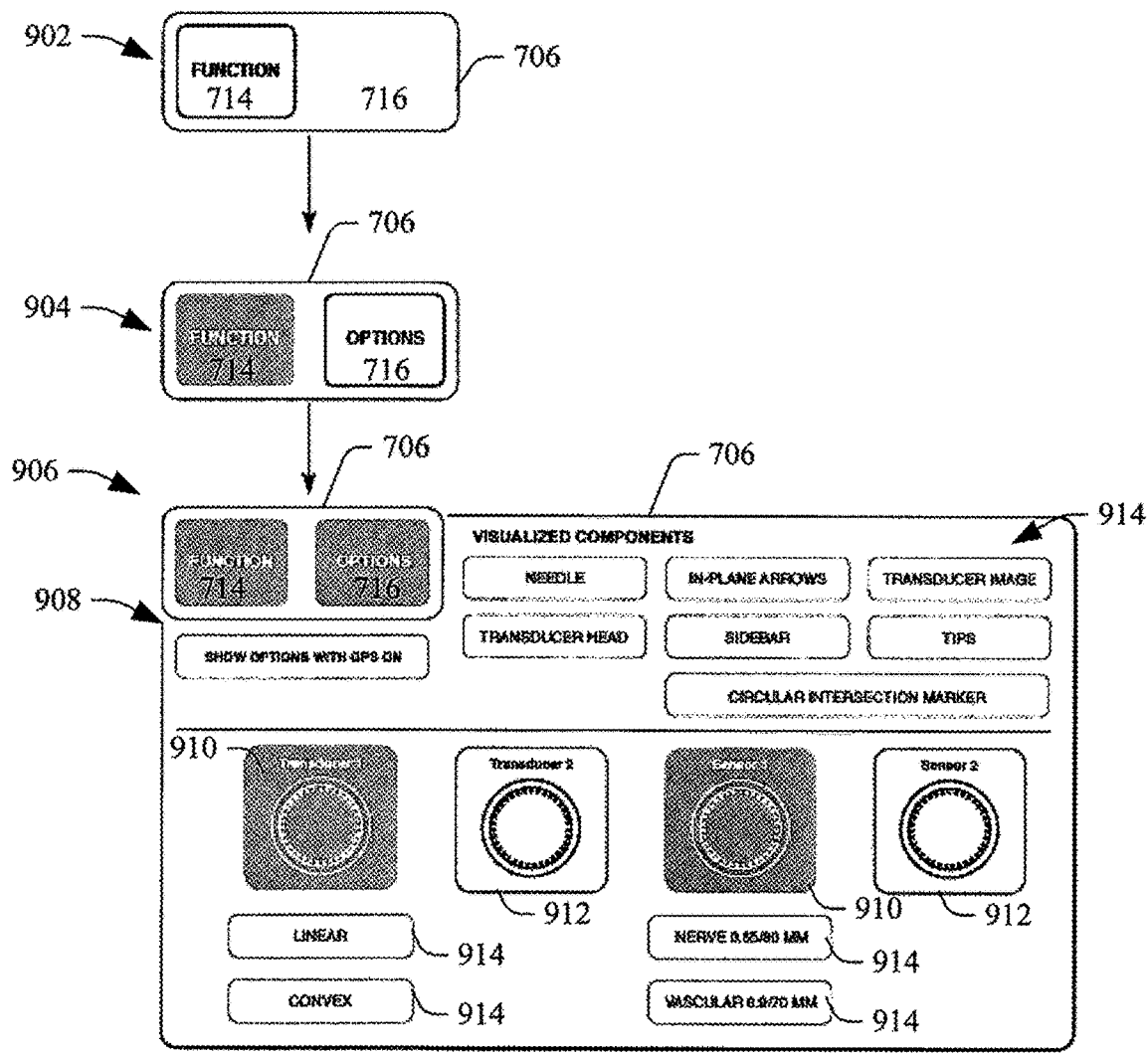
FIG. 9 illustrates interaction of controls which display additional controls for the grouping of FIGS. 7 and 8.
Figure 10:
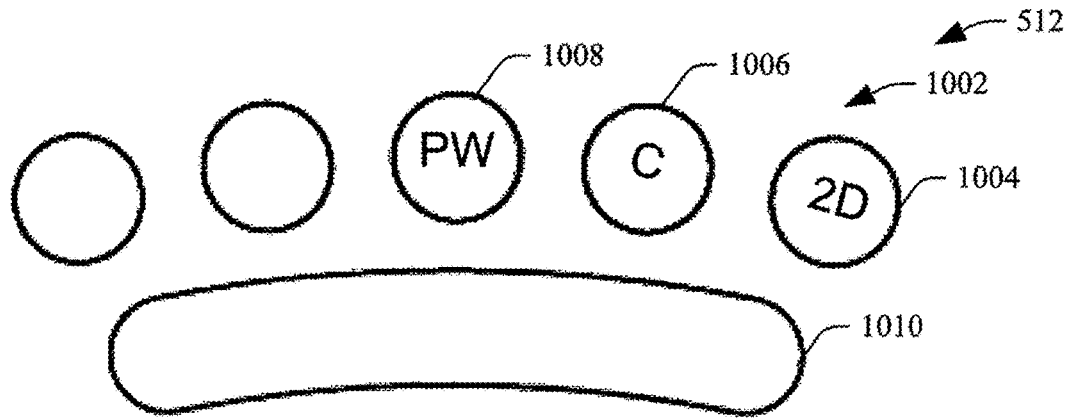
FIG. 10 illustrates a subset of controls within a cluster.

FIG. 9 shows a further example of the grouping 706 of FIGS. 7 and 8. At 902, the controls 714 and 716 are as shown in FIGS. 7 and 8. At 904, the control 714 invoked to transition into the active status, and the control 716, in coordination therewith, automatically transitions to the activatable state. At 906, the control 716 invoked to transition into the active state. In this example, invoking the control 716 results in the touch screen controller 148 constructing and visually displaying a set of extended controls 908. The set of controls 908 is shown with controls 910 in the active state, controls 912 in the activatable state, and controls 914 in the inactive state. Invoking the control 714 to transition to the activatable state at 902 automatically transitions the control 716 to the inactive state like at 902. Changing the state of one or both of the controls 714 and 716 may also transition at least one other control 702 of FIGS. 7 and 8 to another state.

FIGS. 10, 11, 12, 13, 14, 15 and 16 illustrate example interaction within a sub-portion 1002 of the primary cluster 512. Initially referring to FIG. 10, at least a sub-set of controls 1004, 1006 and 1008 are configured to operate in single, duplex or triplex mode. The control 1004 controls a "2D" mode operation, a control 1006 controls a "color" mode operation, and a control 1008 controls a "pulse wave" mode operation. In other example, the controls 1004, 1006 and 1008 can control other operations. The controls 1004, 1006 and 1008 are spatially grouped together and can be invoked for simultaneous operation of their respective modes. In single mode, only one of the controls 1004, 1006 and 1008 is active. In duplex mode, two of the controls 1004, 1006 and 1008 are active. In triplex mode, all three of the controls 1004, 1006 and 1008 are active. A control 1010 controls a gain for the in focus mode.

Figure 11:
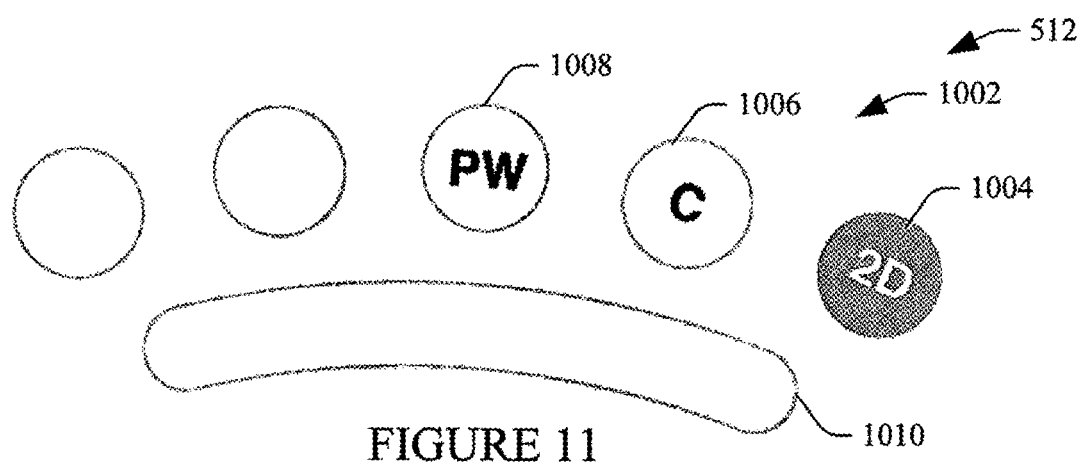
FIG. 11 illustrate single control mode in connection with FIG. 10.
Figure 12:
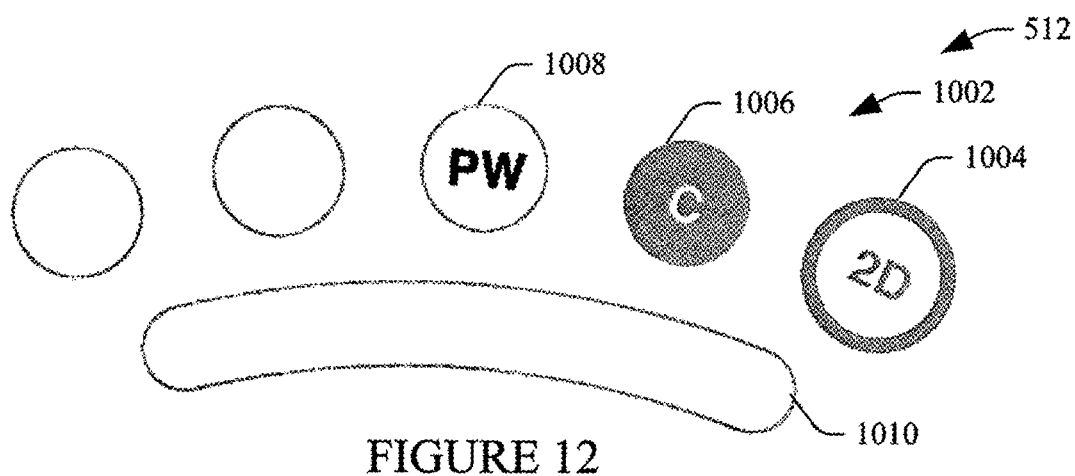
FIG. 12 illustrates duplex control mode in connection with FIG. 10.
Figure 13:
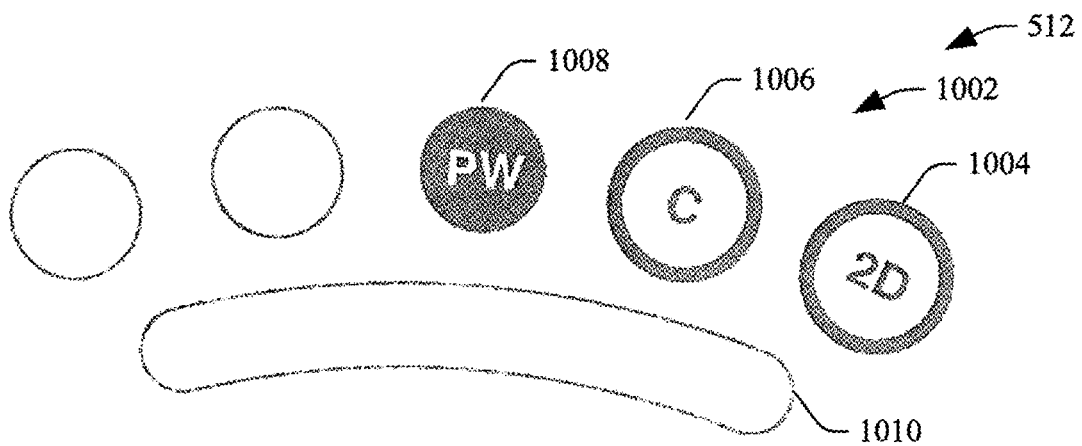
FIG. 13 illustrates triplex control mode in connection with FIG. 10.
Figure 14:
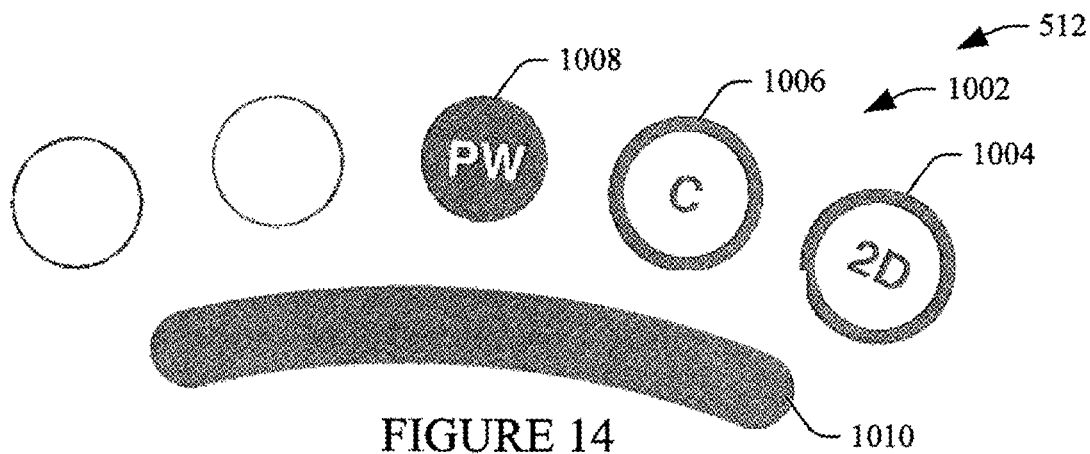
FIGS. 14-16 illustrate a common control shared across the controls in triplex mode.
Figure 15:
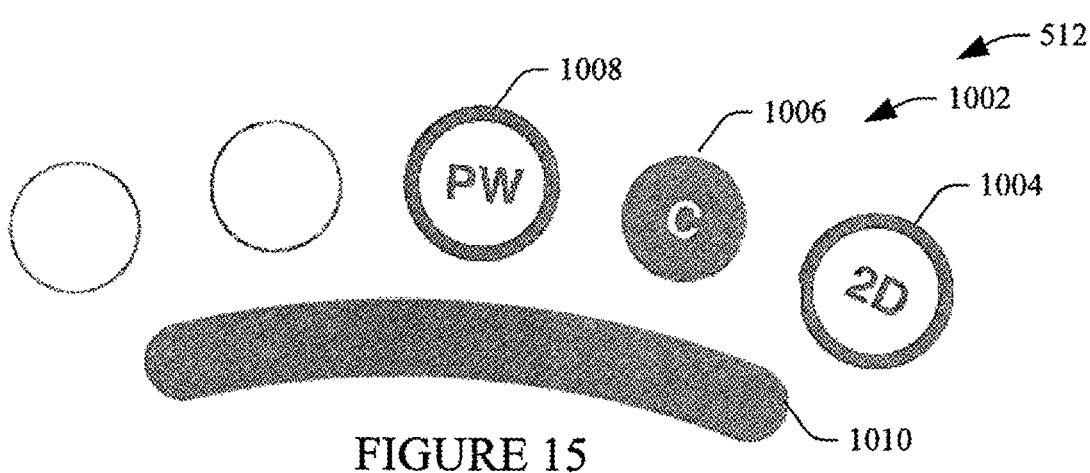
Figure 16:
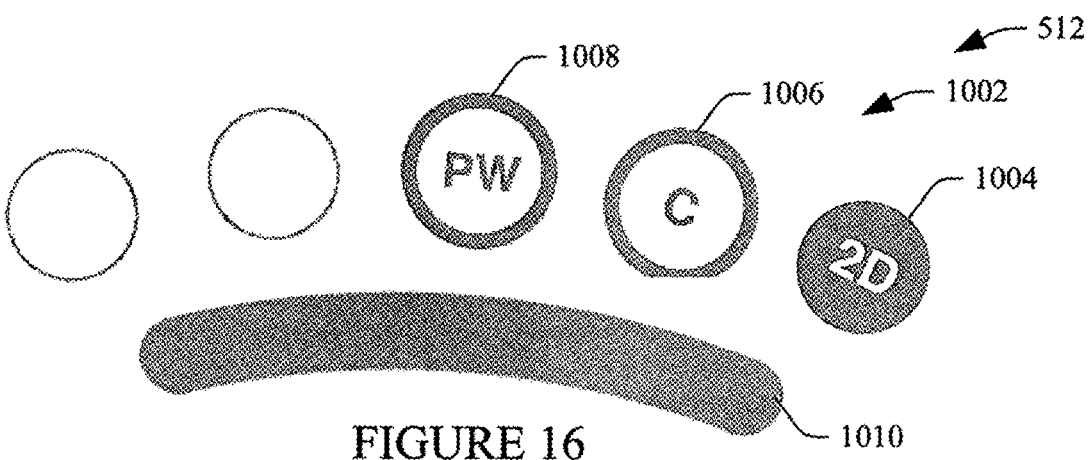

With duplex and triplex modes, the active control of the multiple active controls that is currently being used is the active in focus control. In FIG. 11, the control 1004 is the active control. The controls 1006 and 1008 are activatable. In FIG. 12, the controls 1004 and 1006 are both active with the control 1006 being the active in focus control. The control 1008 is activatable. In FIG. 13, the controls 1004, 1006 and 1008 are all active with the control 1008 being the active in focus control. FIG. 14 is similar to FIG. 13 except that the common control 1010 is active for control 1008. In FIG. 15, the controls 1004, 1006 and 1008 are all active with the control 1006 being the active in focus control and common control 1010 is active for control 1006. In FIG. 16, the controls 1004, 1006 and 1008 are all active with the control 1004 being the active in focus control and common control 1010 is active for control 1004. The common control 1010, in this example, represents a control shared across the controls 1004-1008 to control a gain and/or other parameter for each of the controls 1004, 1006 and 1008.

Figure 17:
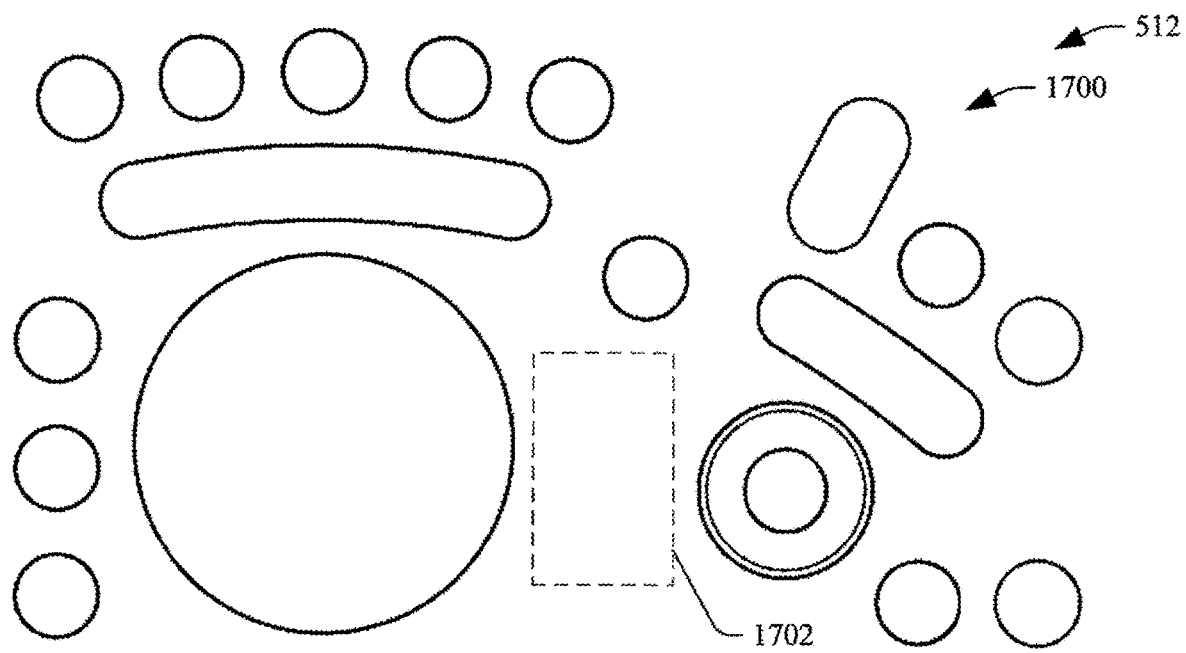
FIGS. 17 and 18 illustrate interaction which displays additional soft controls.
Figure 18:
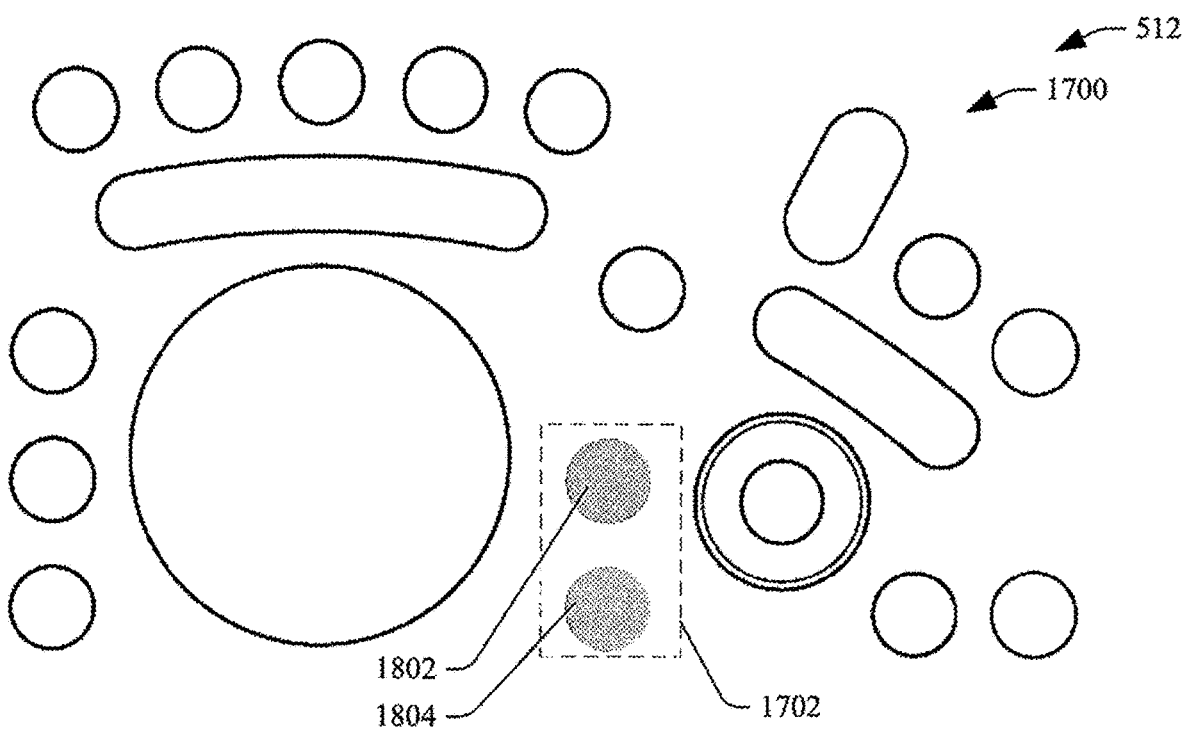

FIGS. 17 and 18 illustrate another example interaction within the primary cluster 512. In FIG. 17, the primary cluster 512 includes controls 1700 and a region 1702 in which the touch screen controller 148 can render nothing or a visible soft control. In one instance, the default configuration is no soft control. As shown in FIG. 18, the touch screen controller 148 renders one or more soft controls 1802 and 1804 in the region 1702 in response to invocation of a control of the controls 1700. The soft controls 1802 and 1804 provide extended functionality for the cluster. In other embodiments, the region 1702 could be located elsewhere on the touch panel 124. Furthermore, the touch panel 124 may include more than one region 1702. All of the controls 1700 may not include extended functionality. In such instance, nothing or other information can be rendered in the region 1702.

Figure 19:
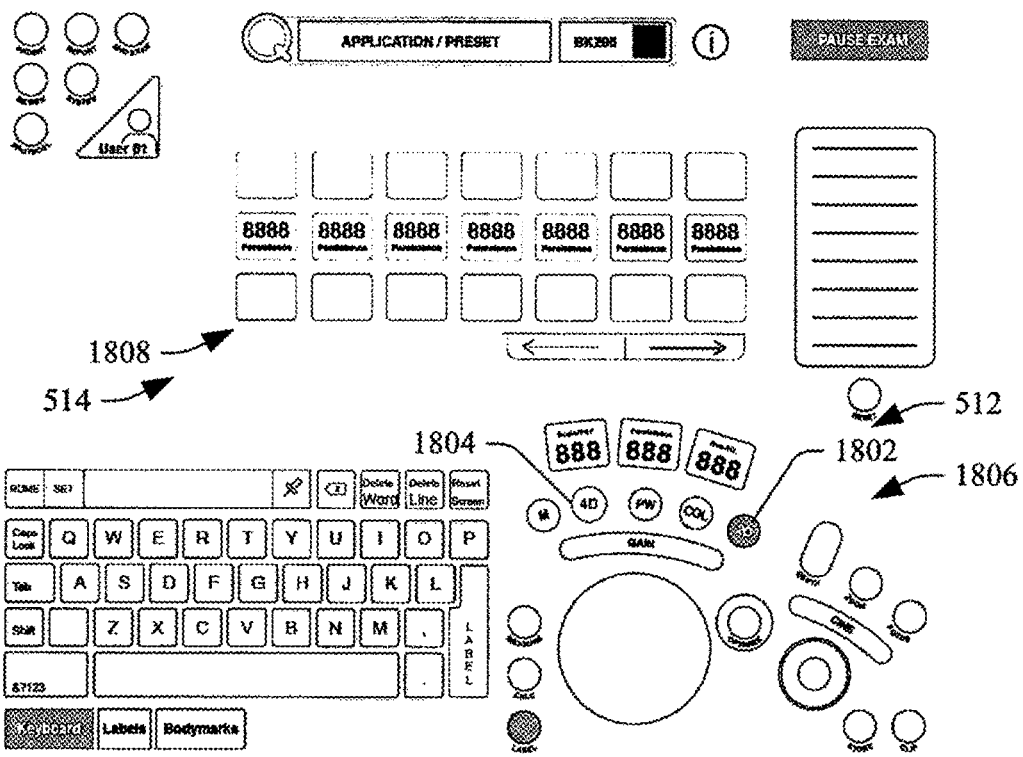
FIGS. 19 and 20 illustrate interaction between controls of a same cluster and between different clusters.
Figure 20:
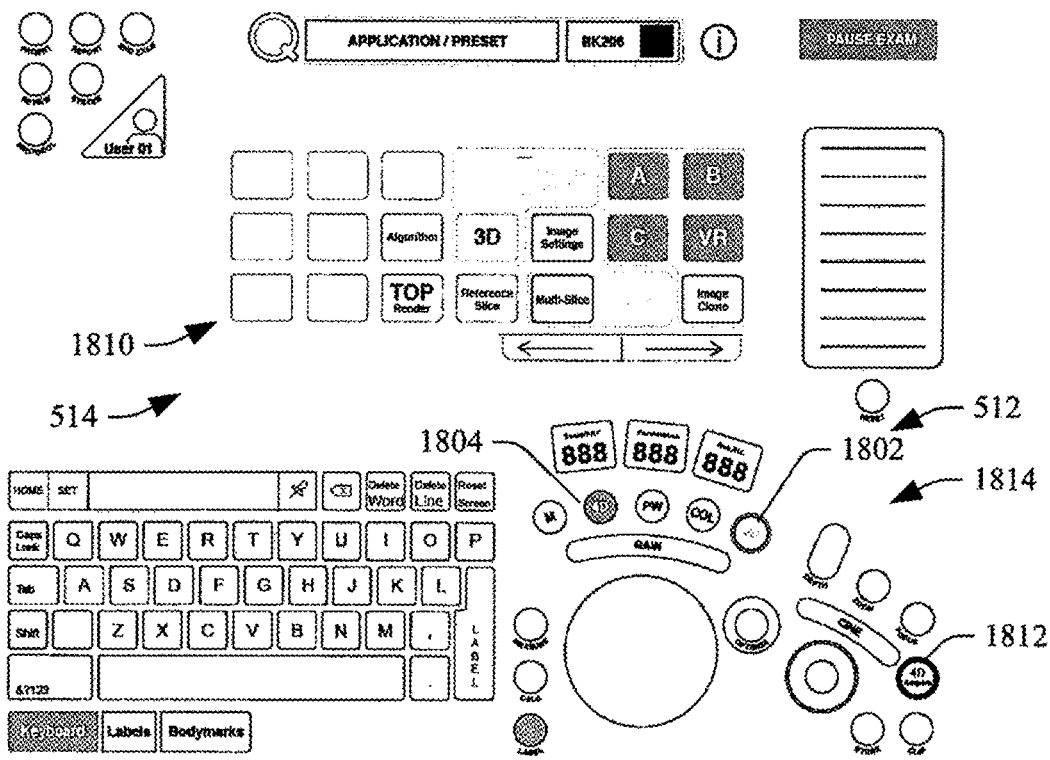

FIGS. 19 and 20 illustrate example interaction within the primary cluster 512 and between the primary cluster 512 and the context cluster 514. In FIG. 19, a control 1802 is the active control. In this example, the control 1802 controls an operation of the 2D mode. A control 1804 is activatable. The primary cluster 512 includes a first set of controls 1806, and the context cluster 514 includes a second set of controls 1808. FIG. 20 shows that when the control 1804 is invoked to be active in focus, at least a sub-set of the controls in the context cluster 514 changes to the context of the mode operated by the control 1804, for example, 4D controls. The context cluster 514 now includes a different set of controls 1810. This represents an example of interaction between the primary cluster 512 and the context cluster 514. Additionally, the touch screen controller 148 renders a soft control 1812 on the touch panel 124 in the primary cluster 512. The primary cluster 512 now includes a different set of controls 1814. This represents an example of interaction within the primary cluster 512.

Figure 21:
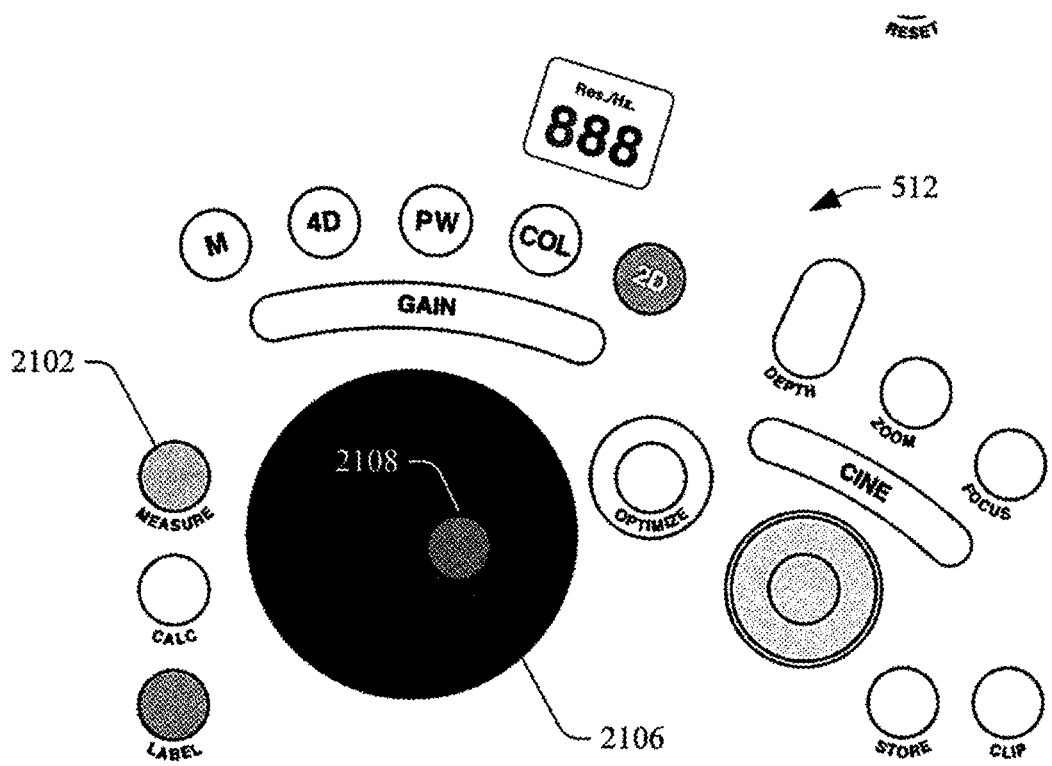
FIGS. 21-24 illustrate interaction within a cluster in connection with measurement controls.
Figure 22:
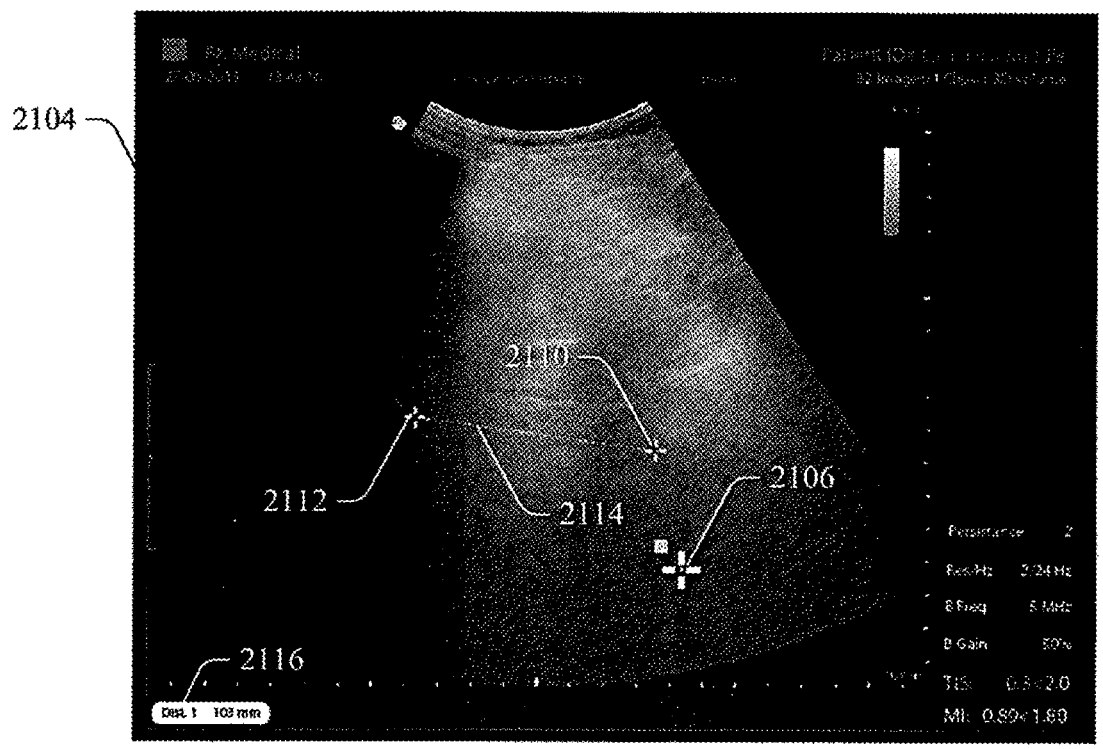

FIGS. 21-24 illustrate an example of the primary cluster 512 in connection with taking measurements and interaction within the primary cluster 512. In FIG. 21, a control 2102 which is configured to control measurement functions is active. FIG. 22 shows an image 2104. The image 2104 can be displayed by the display monitor 112 and/or the touch screen user interface 122. With reference to FIGS. 21 and 22, a control 2106 (such as a trackball control) controls a spatial location of cursor 2106 that is superimposed over the image. A gesture such as a finger tap or press on the control 2106 (shown by 2108) places a mark 2110 on the image 2104. The mark 2110 represents one of two marks identifying end points for a length measurement. FIG. 22 also shows a second mark 2112 with a line 2114 between the two marks 2110 and 2112 indicating which two marks are the end points for a measurement, which is displayed in measurement display 2116.

Figure 23:
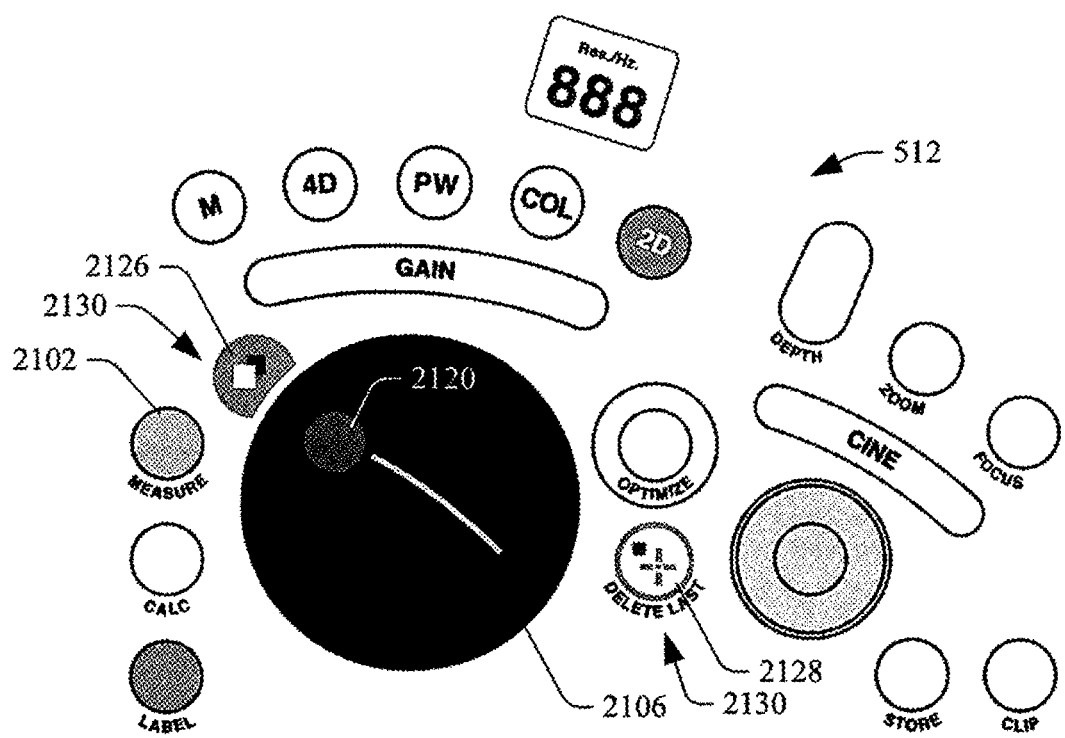
Figure 24:
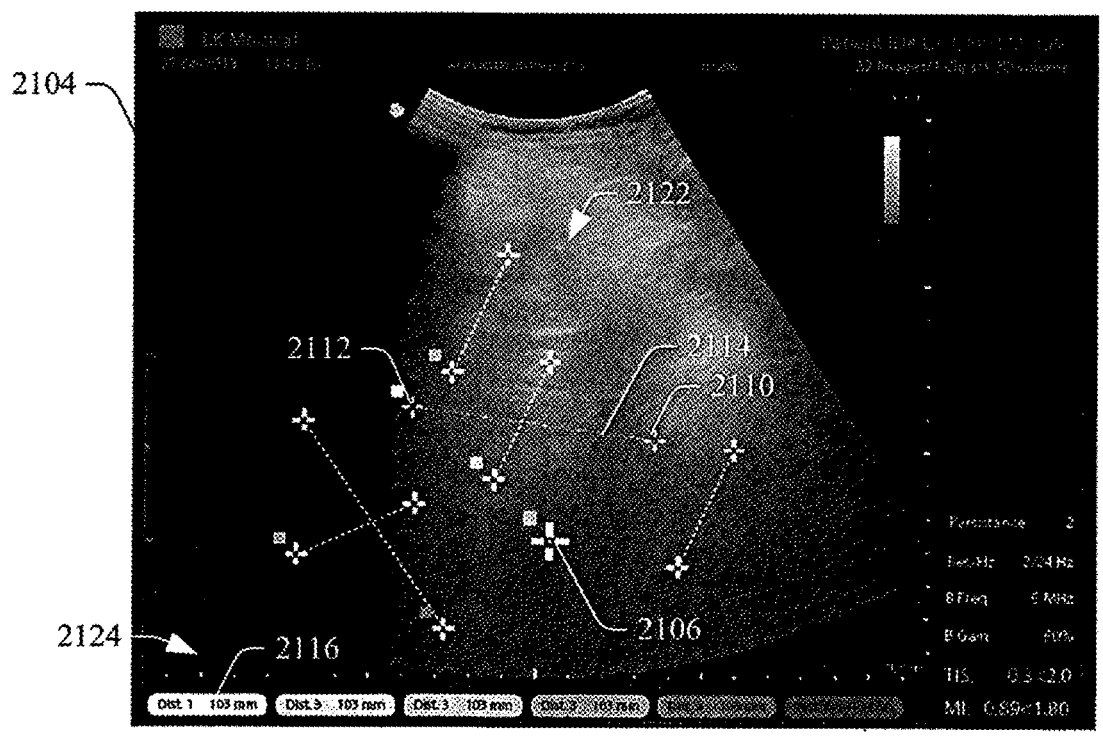

FIG. 23 shows a second gesture such as a finger tap or press on the control 2106 (shown by 2120), which places the second mark 2112 on the image 2104. The gesture can be made after swiping across the control 2106 or removing physical contact and the establishing physical contact at 2120. In the illustrated example, a plurality of pairs of marks 2122 is illustrated along visual presentation of the corresponding measurements 2124. In response to adding at least one mark, the touch screen controller 148 renders a soft control 2128 in a region 2130, which is similar to the region 1702 of FIGS. 17 and 18 in that the touch screen controller 148 can render different visible soft controls in the region 2130, for example, based on the active mode of operation or no visible soft control. In this example, the touch screen controller 148 renders a soft control 2128 which, if invoked, deletes the last measurement mark.

With further reference to FIGS. 22 and 23, in response to adding at least two marks, the touch screen controller 148 renders a soft control 2126 in another region 2130 on the touch panel 124 in the primary cluster 512. In the illustrated example, the soft control 2126 is adjacent to the control 2106. However, other locations are contemplated herein. In the illustrated example, the soft control 2126 is configured to toggle through the measurement marks to control which of the measurement marks is editable at any given time. In operation, the user performs a gesture (e.g., a tap) on the soft control 2126. With each tap, the measurement mark which is editable changes to another measurement mark. The sequence may be determined on a temporal basis, such as the time a measurement mark was created relative to other measurement marks and/or otherwise. An editable measurement mark can be moved. The measurement mark can be saved and/or stored along with the image 2104.

Figure 25:
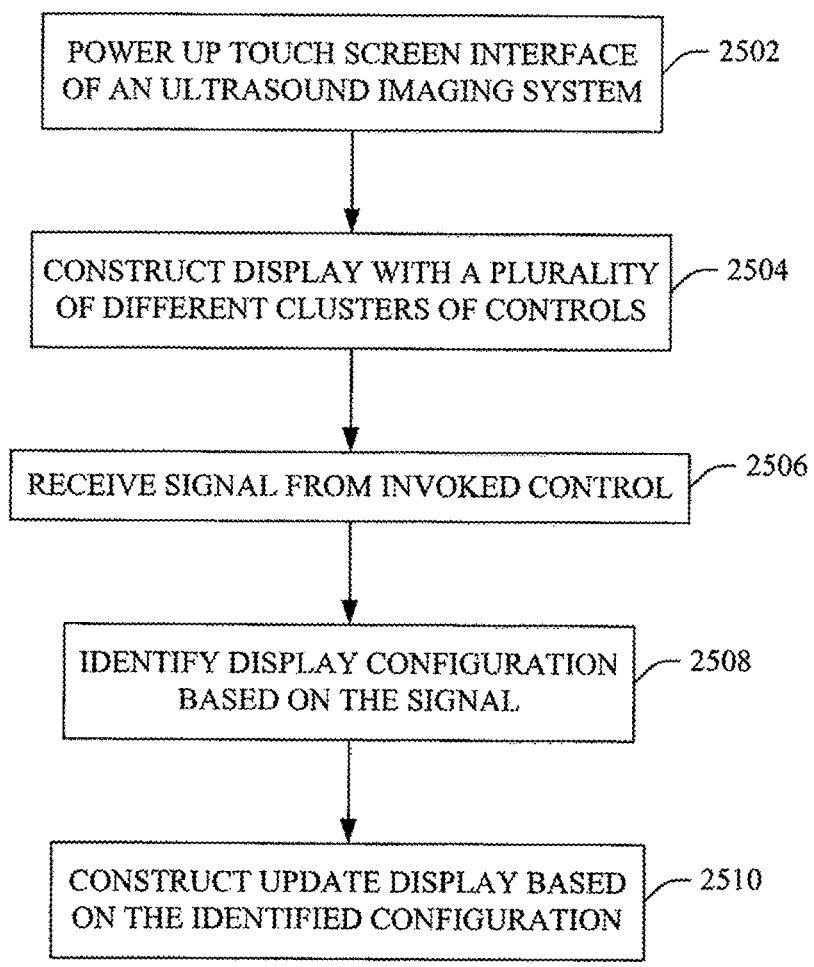
FIG. 25 illustrates example method in accordance with the description herein.

FIG. 25 illustrates example method in accordance with one or more of the embodiments described herein.

It is to be appreciated that the ordering of the below acts is for explanatory purposes and not limiting. As such, other orderings are also contemplated herein. In addition, one or more of the acts may be omitted and/or one or more other acts may be included.

At 2502, a touch screen interface of an ultrasound imaging system is turned on.

At 2504, a display, including a plurality of different clusters of controls, is constructed on a touch panel of the touch screen interface.

At 2506, a signal is received from the control in response to invocation of the control.

At 2508, a display configuration is identified based on the signal.

At 2510, an update display is constructed based on the identified configuration.

In the updated display, at least one of another control of the cluster is automatically changed or a control of another cluster is automatically changed. As described herein, this may include changing a state of another control of the cluster, changing a set of controls of the cluster or the other cluster, displaying an additional set of soft controls, etc.

At least a portion of the methods discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
    receiving a signal from a first touch screen control in response to invocation of the first touch screen control, wherein the first touch screen control is a control from a first cluster of touch screen controls of a plurality of different clusters of touch screen controls of an ultrasound imaging system touch screen user interface;
    identifying a type of the first touch screen control based on the signal;
    obtaining a control configuration for the touch screen controls based on the type of control;
    constructing a control layout for the touch screen user interface based on the configuration, wherein constructing the control layout includes changing a context of functions previously assigned to a spatially fixed set of controls and graphical indicators of those functions from a first set of functions and graphical indicators for a previously actuated touch screen control to a second different set of functions and graphical indicators for the first touch screen control; and
    visually rendering the control layout via the touch screen user interface.

2. The method of claim 1, wherein a control is configured to be in one of an active state, an activatable state, or an inactive state.

3. The method of claim 2, further comprising: automatically transitioning the second touch screen control of the first cluster to the inactive state in response to the first touch screen control transitioning to the inactive state.

4. The method of claim 1, wherein visually rendering the control layout includes transitioning a second touch screen control of the first cluster to a different state from a state of the second control prior to invocation of the first touch screen control.

5. The method of claim 4, further comprising: automatically transitioning the second touch screen control of the first cluster from the inactive state to the activatable state only in response to the first touch screen control of the first cluster transitioning to the active state.

6. The method of claim 4, further comprising:
    receiving a second signal from the second touch screen control; and
    visually rendering the second touch screen control in a same state as the first touch screen control.

7. The method of claim 6, further comprising:
    visually rendering an extended set of controls for the first cluster in response to the second signal by adding a new control to existing controls of the set of controls.

8. The method of claim 4, wherein the first and second controls are part of a same sub-grouping of related controls of the first cluster of touch screen controls and the second touch screen control controls a sub-function of the functions controlled by the controls of the first cluster of controls.

9. The method of claim 1, further comprising:
    receiving a third signal from a third touch screen control of the first cluster in response to invocation of the third touch screen control; and
    rendering the first and third touch screen controls in a same state, wherein the first and third touchscreen controls are independent controls and the state is the active state.

10. The method of claim 9, further comprising: visually rendering a single control of the first cluster configured to control a same function for the first and third touch screen controls.

11. The method of claim 9, further comprising:
    receiving a fourth signal from a fourth touch screen control of the first cluster in response to invocation of the third touch screen control; and
    rendering the first, third and fourth touch screen control in a same state, wherein the first, third and fourth touchscreen controls are independent controls and the state is the active state.

12. The method of claim 11, further comprising: visually rendering a single control of the first cluster configured to control a same function for the first, third and fourth touch screen controls.

13. The method of claim 1, wherein visually rendering the control layout includes transitioning a second touch screen control of a second different cluster to a different state from a state of the second control prior to invocation of the first touch screen control.

14. The method of claim 1, wherein the visually rendering of the control layout includes changing a type of another control of the first cluster of touch screen controls.

15. The method of claim 1, wherein the visually rendering of the control layout includes changing a type of a control of a different cluster of touch screen controls.

16. The method of claim 1, further comprising:
visually rendering a soft control on the touch screen user interface in response to invocation of the first touch screen control from the first cluster.

17. The method of claim 16, where the soft control includes additional controls for the type of control.

18. The method of claim 17, wherein the additional control is configured to control an editing operation of a measurement landmark on an ultrasound image displayed via a display of the ultrasound imaging system.

19. The method of claim 18, wherein the editing operation moves a location of a saved measurement landmark to a different location on the image in response to a user input.

20. A method, comprising:
receiving a signal from a first touch screen control in response to invocation of the first touch screen control, wherein the first touch screen control is a control from a first cluster of touch screen controls of a plurality of different clusters of touch screen controls of an ultrasound imaging system touch screen user interface;
identifying a type of the first touch screen control based on the signal;
obtaining a control configuration for the touch screen controls based on the type of control;
constructing a control layout for the touch screen user interface based on the configuration, wherein constructing the control layout includes changing a context of functions previously assigned to a spatially fixed set of controls and graphical indicators of those functions from a first set of functions and graphical indicators for a previously actuated touch screen control to a second different set of functions and graphical indicators for the first touch screen control;
visually rendering the control layout via the touch screen user interface;
receiving a second signal from a second touch screen control of the first cluster in response to invocation of the second touch screen control; and
visually rendering the first and second touch screen controls in a same state, wherein the first and second touchscreen controls are independent controls and the state is the active state.

21. The method of claim 20, wherein visually rendering the control layout includes transitioning the second touch screen control of the first cluster to a different state from a state of the second control prior to invocation of the first touch screen control.

22. The method of claim 21, further comprising:
automatically transitioning the second touch screen control of the first cluster from the inactive state to the activatable state only in response to the first touch screen control of the first cluster transitioning to the active state.

23. The method of claim 21, further comprising:
automatically transitioning the second touch screen control of the first cluster to the inactive state in response to the first touch screen control transitioning to the inactive state.

24. The method of claim 20, further comprising:
receiving a third signal from a third touch screen control of the first cluster in response to invocation of the third touch screen control; and
rendering the first, second and third touch screen controls in a same state, wherein the first, second and third touchscreen controls are independent controls and the state is the active state.

25. The method of claim 24, further comprising:
visually rendering a single control of the first cluster configured to control a same function for the first, second and third touch screen controls.

26. An ultrasound imaging system, comprising:
a touch screen user interface, including a plurality of different clusters of touch screen controls; and
a console, including a touch screen controller;
wherein the touch screen controller is configured to:
receive a signal from a first touch screen control from a first cluster of touch screen controls of the plurality of different clusters in response to invocation of the first touch screen control;
identify a type of the first touch screen control based on the signal;
obtain a control configuration for the touch screen controls based on the type of control;
construct a control layout for the touch screen user interface based on the configuration, wherein constructing the control layout includes changing functions previously assigned to a spatially fixed set of controls from a first set of functions for a previously actuated touch screen control to a second different set of functions for the first touch screen control; and
visually render the control layout via the touch screen user interface.

27. The ultrasound imaging system of claim 26, wherein the touch screen controller is configured to:
receive a second signal from a second touch screen control of the first cluster in response to invocation of the second touch screen control; and
visually render the first and second touch screen controls in a same state, wherein the first and second touchscreen controls are independent controls and the state is the active state.

28. The ultrasound imaging system of claim 26, wherein the touch screen controller is configured to:
receive a third signal from a third touch screen control of the first cluster in response to invocation of the third touch screen control; and
visually render the first, second and third touch screen controls in a same state, wherein the first, second and third touchscreen controls are independent controls and the state is the active state.

29. The ultrasound imaging system of claim 28, wherein the touch screen controller is configured to:
visually render a single control of the first cluster configured to control a same function for the first, second and third touch screen controls.

30. The ultrasound imaging system of claim 29, wherein the touch screen controller is configured to:
visually render a single control of the first cluster configured to control a same function for the first and second touch screen controls.

31. The ultrasound imaging system of claim 26, wherein the touch screen controller is configured to:

change a type of a control of a different cluster of touch screen controls.

* * * * *